United States Patent [19]
Black

[11] Patent Number: 5,993,654
[45] Date of Patent: Nov. 30, 1999

[54] PRESSURIZED LIQUID DELIVERY APPARATUS

[75] Inventor: Bruce Black, Napa, Calif.

[73] Assignee: Eldex Laboratories, Inc., Napa, Calif.

[21] Appl. No.: 09/159,845

[22] Filed: Sep. 24, 1998

[51] Int. Cl.⁶ .................................................. B01D 15/08
[52] U.S. Cl. ...................... 210/198.2; 210/101; 210/656; 417/2; 417/26; 417/44.2
[58] Field of Search .................................. 210/656, 659, 210/101, 198.2; 417/2, 3, 43, 44.2, 26

[56] References Cited

U.S. PATENT DOCUMENTS

| | | | |
|---|---|---|---|
| 3,917,531 | 11/1975 | Magnussen | 210/198.2 |
| 4,043,906 | 8/1977 | Helmer | 210/31 C |
| 4,347,131 | 8/1982 | Brownlee | 210/101 |
| 4,422,942 | 12/1983 | Allington | 210/659 |
| 4,457,846 | 7/1984 | Munk | 210/656 |
| 4,592,842 | 6/1986 | Tomlinson | 210/198.2 |
| 4,595,496 | 6/1986 | Carson | 210/198.2 |
| 4,767,279 | 8/1988 | Dourdeville | 210/198.2 |
| 4,883,409 | 11/1989 | Strohmeier | 210/101 |
| 5,393,434 | 2/1995 | Hutchins | 210/198.2 |
| 5,637,208 | 6/1997 | Dourdeville | 210/90 |
| 5,897,781 | 4/1999 | Dourdeville | 210/656 |

*Primary Examiner*—Ernest G. Therkorn
*Attorney, Agent, or Firm*—Thomason, Moser and Patterson

[57] ABSTRACT

First liquid pumping apparatus for containing a first quantity of first liquid, second liquid pumping apparatus for containing a second quantity of second liquid and control apparatus for alternately connecting the first liquid pumping apparatus and second liquid pumping apparatus to pressurized liquid utilization apparatus and for causing the first and second liquid pumping apparatus to alternately deliver the respective liquids to the liquid utilization apparatus at a substantially constant flow or substantially constant pressure; the first and second liquids may be the same liquid or different liquids.

12 Claims, 5 Drawing Sheets

PRESSURIZED LIQUID DELIVERY APPARATUS

BACKGROUND OF THE INVENTION

1. Field of the Invention

This invention relates generally to apparatus for alternately delivering pre-pressurized first and second liquids to liquid utilization apparatus at either a constant flow or at a constant pressure, and more particularly relates to apparatus for alternately delivering pre-pressurized solvent and pre-pressurized wash at a constant flow to a liquid system.

2. Description of the Background Art

With regard to liquid chromatography, typical prior art liquid delivery or pumping apparatus for delivering pressurized (typically referred to in the art as pre-pressurized) solvent to a liquid chromatography system for elution typically utilizes a syringe pump for delivering the pre-pressurized solvent to the liquid chromatography system. The typical prior art syringe pump includes a cylinder, piston and associated accessories for operation. The syringe pump cylinder contains a limited quantity of solvent which is pressurized and expelled to the liquid chromatography system upon being connected thereto. This is inherently a batch operation, and upon the limited quantity of solvent in the syringe pump being expelled, the syringe pump must be de-pressurized, refilled and re-pre-pressurized to deliver further solvent to the liquid chromatography system, and this causes the liquid chromatography system to be pressurized, de-pressurized and re-pressurized. This problem of pressurization, de-pressurization and re-pressurization associated with liquid chromatography systems is further compounded when a limited quantity of pressurized solvent is delivered to the system, the system is de-pressurized, a limited quantity of pre-pressurized wash is delivered to the system, the system is de-pressurized and pressurized solvent is again delivered to the system and these operations are further repeated. The major disadvantage to these batch operations is that they can be undesirably time consuming and another major disadvantage is that you expose the liquid chromatography system to continual pressurization, de-pressurization and re-pressurization cycles which is believed, at least to a certain extent, to damage or shorten the life of the liquid chromatography system components, particularly the liquid chromatography column.

Numerous pumping systems and apparatus, particularly those including syringe pumps, are known to the prior art for delivering pressurized solvent to liquid chromatography apparatus systems under isocratic and/or gradient elusion conditions. U.S. Pat. No. 4,347,131 issued Aug. 31, 1982 to Robert Brownlee discloses a liquid chromatographic pump module for liquid chromatography for delivering the mobile phase to a separation column under high pressure and which includes a cylinder containing a plunger forming a syringe pump with a seal disposed between the plunger and the cylinder and which further includes two positive action valves for connecting the output of the pump to either a reservoir of the mobile phase or to a sample injection valve. This patent is hereby incorporated herein as if fully reproduced herein. U.S. Pat. No. 5,637,208 issued Jan. 10, 1997 to Theodore A. Dourdeville discloses a solvent pumping system for chromatography and for continuously delivering fluid at a selected flow rate to a receiving system such as a high-performance liquid chromatography system. The solvent pumping system includes first and second liquid pumping units each comprising a syringe and a valve. The first and second liquid pumping units are in fluid communication with one another and are capable of independent actuation. The individual valves are arranged to isolate either the first syringe or the second syringe, respectively, from the receiving system while at least one of the syringes remains in fluid communication with the receiving system whereby system pressure can be continuously monitored and the selected system flow rate maintained. The pumping system includes a controller which receives inputs from first and second pressure sensors, associated respectively with the first and second liquid pumping units and the controller activates in response to the inputs of the first and second syringes individually and also activates the first and second valves individually such that when fluid communication is established between the isolated syringe and the receiving system substantially no system flow error is said to be produced. The pressure sensor is positioned within each pumping unit permitting a pumping unit which has been refilled off line to perform compression of its cylinder contents without perturbation of the on-line process and which further permits discrimination of the point in the compression cycle where compression has been completed and fluid delivery to the system will commenced.

Another syringe or syringe-type pumping system for delivering solvent to a liquid chromatography system is the Micropro Dual Gradient Pump Model No. HPLC2g available from Eldex Laboratories, Inc., 30 Executive Court, Napa, Calif. 94558-6278, the assignee of the present invention.

Although at least certain of the above-noted prior art syringe pumps for delivering pressurized solvent to a liquid chromatography system for elution are presently commercially acceptable and have worked reasonably well, there still exists a need in the art for a new and improved apparatus which can be embodied as apparatus for alternately delivering pre-pressurized solvent and pre-pressurized wash to a liquid chromatography system at a substantially constant flow and wherein the system experiences substantially no de-pressurization and re-pressurization in switching from the solvent to the wash and back to the solvent.

SUMMARY OF THE INVENTION

It is the object of the present invention to satisfy the foregoing need in the art.

Apparatus satisfying the foregoing need and embodying the present invention may include first pumping apparatus for containing a first quantity of first liquid, second liquid pumping apparatus for containing a second quantity of second liquid and control apparatus for alternately connecting the first pumping apparatus and second liquid pumping apparatus to liquid utilization apparatus and for causing the first and second liquid pumping apparatus to alternately deliver the respective liquids to a liquid utilization apparatus.

DESCRIPTION OF THE PREFERRED EMBODIMENT

Figure 1:
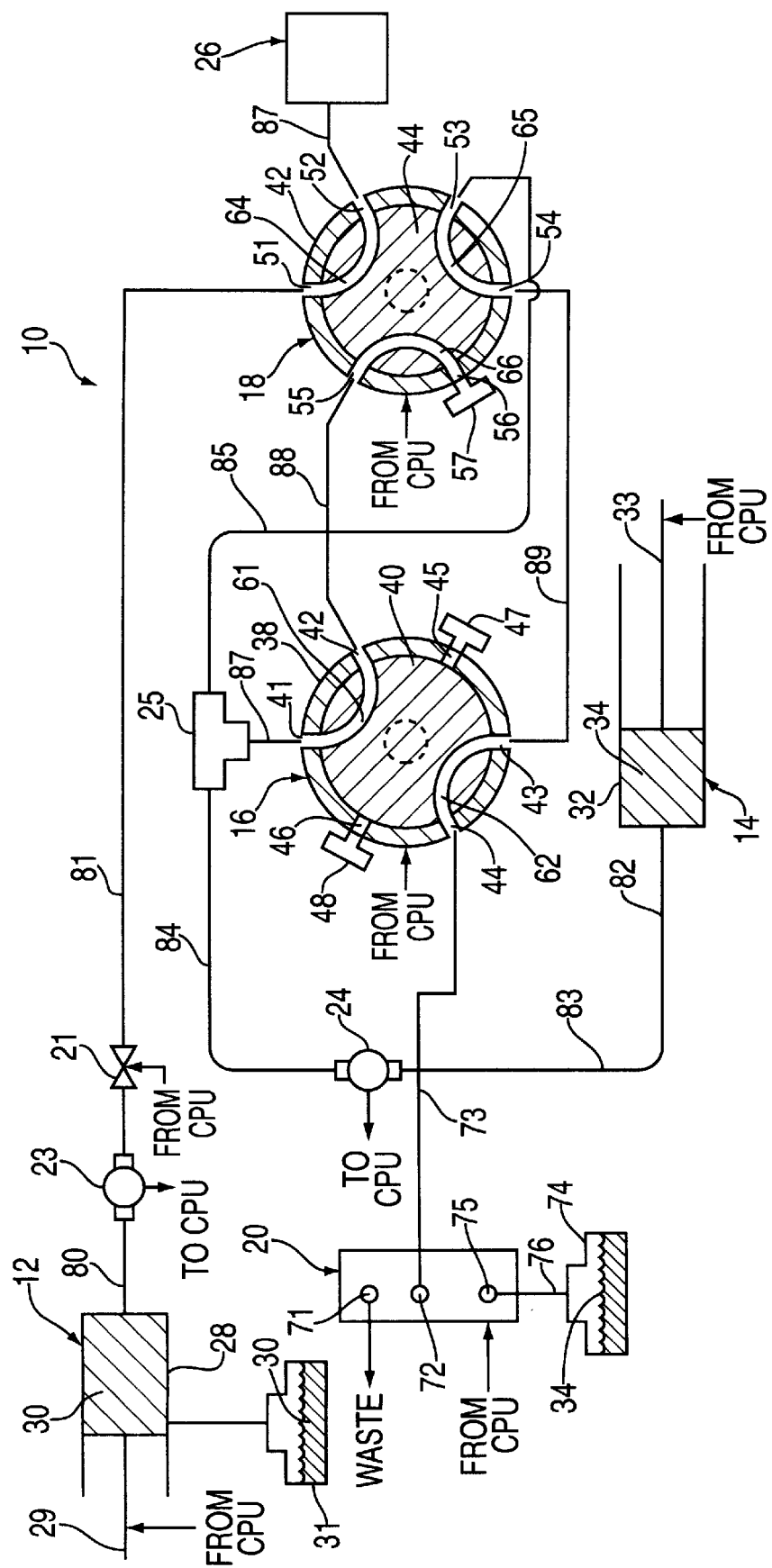
FIGS. 1–3 illustrate, diagrammatically and respectively, three stages of operation of apparatus embodying the present invention and each figure illustrates the various positions occupied by various elements comprising the apparatus embodying the present invention during the different stages of operation, such apparatus includes syringe pumps which are illustrated diagrammatically as including a cylinder and a plunger mounted for sliding reciprocal movement within the cylinder.

The present invention, by way of example and not by way of limitation, will be described embodied as apparatus including syringe pumps operated to alternately deliver pre-pressurized solvent and a pre-pressurized wash to a liquid chromatography system at a substantially constant flow. Although wash and solvent liquids are illustratively described, any liquids that are useful in performing liquid chromatography or similar processes may be used.

Referring now in detail to FIGS. 1–4, apparatus embodying the present invention is indicated by general numerical designation 10 and includes a primary or first syringe pump indicated by general numerical designation 12, a second syringe pump indicated by general numerical designation 14, a first rotary valve indicated by general numerical designation 16, a second rotary valve indicated by general numerical designation 18, a switching valve indicated by general numerical designation 20, an on-off valve 21, a first transducer 23, a second transducer 24, and a T-connection 25. It will be generally understood that the apparatus 10 alternately connects the primary syringe pump 12 and syringe pump 14 to the liquid chromatography system indicated diagrammatically in FIG. 1 by general numerical designation 26 so as to cause the two syringe pumps to alternately deliver pre-pressurized solvent and a pre-pressurized wash to the liquid chromatography system at a substantially constant flow. It will be understood that the liquid chromatography system 26 includes a liquid chromatography column not shown.

The syringe pump 12 may be, for example, the single syringe pump 28 disclosed in U.S. Pat. No. 4,347,131 incorporated hereinabove, the single or double syringe or syringe pumps disclosed in U.S. Pat. No. 5,637,208 incorporated hereinabove, the Micropro Dual Gradient Pump Model HPLC2g available from Eldex Laboratories, Inc. referred to hereinabove, or other suitable liquid delivery means or liquid pumping means known to the art. Diagrammatically, or illustratively, it will be understood that the syringe pump 12 includes a cylinder 28 and a plunger 29 mounted for slidable reciprocal movement into and out of the cylinder to pre-pressurize and expel solvent 30 (a liquid) and to draw the solvent 30 into the cylinder from a suitable solvent supply or reservoir 31 as described below. The syringe pump 14 may be, for example, the syringe pump 28 disclosed in U.S. Pat. No. 4,347,131 incorporated herein or the single syringe or syringe pump disclosed in U.S. Pat. No. 5,637,208 incorporated herein or other suitable syringe pumps of the type known to the art. Diagrammatically, or illustratively, it will be understood that syringe pump 14 includes a cylinder 32 and a plunger 33 mounted for sliding reciprocal movement into and out of the cylinder to pre-pressurize and expel wash 34 (a liquid) and to draw the wash 34 into the cylinder as described below. It will be understood, and as is known to those skilled in the art, that such syringe pumps may be operated to provide liquid at either a constant flow or at a constant pressure. Accordingly, it will be understood that apparatus embodying the present invention can be seen to alternatively supply pre-pressurized solvent and pre-pressurized wash to a liquid chromatography system at a constant pressure.

Rotary valves 16 and 18 may be, for example, rotary valve Model C2-2006 available from Valco Instruments, Inc., Houston, Tex. 77255 and which rotary valve includes a stationary, hollow, outer cylinder providing six ports and an inner rotor residing rotatably in the cylinder and providing three internal liquid paths; alternatively, the rotary valves 16 and 18 may be other rotary valves known to the art which include an outer cylinder providing a plurality of liquid ports and an inner rotor providing a plurality of internal fluid paths and which valves may be structured, or their structures modified, in accordance with the present invention. Accordingly, it will be understood that rotary valve 16 includes a stationary, hollow, outer cylinder 38 and an inner rotor 40 and that rotary valve 18 includes a stationary, hollow, outer cylinder 42 and an inner rotor 44 resident rotatably within an outer cylinder 42. It will be understood that in the present invention the outer cylinder 38 of rotary valve 16 is only required to have four ports, ports 41, 42 and 43, and that in the event a commercially available rotary valve is used having six ports opposed ports 45 and 46 will be suitably plugged for non-use by respective plugs 47 and 48. Similarly, in the present invention, the outer cylinder 42 of rotary valve 18 is only required to have five ports, ports 51, 52, 53, 54 and 55, and if a commercially available rotary valve is used including an outer cylinder including six ports, the sixth port, port 56, will be suitably plugged such as by plug 57. Rotor 40 of rotary valve 16 in the present invention is only required to have two internal liquid paths, internal liquid paths 61 and 62, and hence if a commercially available rotary valve having more than two internal paths is used for rotary valve 16, the rotor will be modified or replaced as shown to include only the two internal liquid paths 61 and 62. The inner rotor 44 of rotary valve 18 in the present invention includes three internal liquid paths 64, 65 and 66.

The switching valve 20 may be, for example, switching valve Model PNLBT032 available from Neptune Research Inc. of West Caldwell, N.J. 07006 or other suitable switching valves known to the art. Switching valve 20 includes a first port 71 connected to waste, a second port 72 connected by liquid transmission line 73 to the port 44 formed in the outer cylinder 38 of rotary valve 16 and a third port 75 connected by liquid transmission line 76 to a suitable wash reservoir 77 containing suitable wash (a liquid) 34.

Transducers 23 and 24 may be a suitable transducer of the type known to the art for sensing the pressure in a liquid and for providing a signal indicative of the pressure sensed.

The pressurized solvent output of the syringe pump 12, indicated diagrammatically by numeral 80, is connected through on-off valve 21, transducer 23 and liquid transmission line 81 to the port 51 formed in the outer cylinder 42 of rotary valve 18. The pressurized liquid output of syringe pump 14 is indicated diagrammatically by numeral 82 and the output of syringe 14 is connected to the port 53 formed in the outer cylinder 42 of rotary valve 18 through the liquid transmission line 83, transducer 24, the liquid transmission line 84, the through connection of the T-connection 25, and liquid transmission line 85. The output of the syringe pump 14 is also connected to the port 41 provided in the outer cylinder 38 of the rotary valve 16 through liquid transmission line 83, transducer 24, liquid transmission line 84, the lateral connection of the T-connection 25 and liquid transmission line 87. The port 42 formed in the outer cylinder 38 of rotary valve 16 is connected to the port 55 formed in the outer cylinder 42 of rotary valve 18 by liquid transmission line 88 and the port 43 formed in the outer cylinder 38 of rotary valve 16 is connected to the port 54 formed in the outer cylinder 42 of rotary valve 18 by liquid transmission line 89. The port 52 formed in the outer cylinder 42 of rotary valve 18 is connected to a liquid chromatography system 26 by the liquid transmission line 87.

Figure 5:
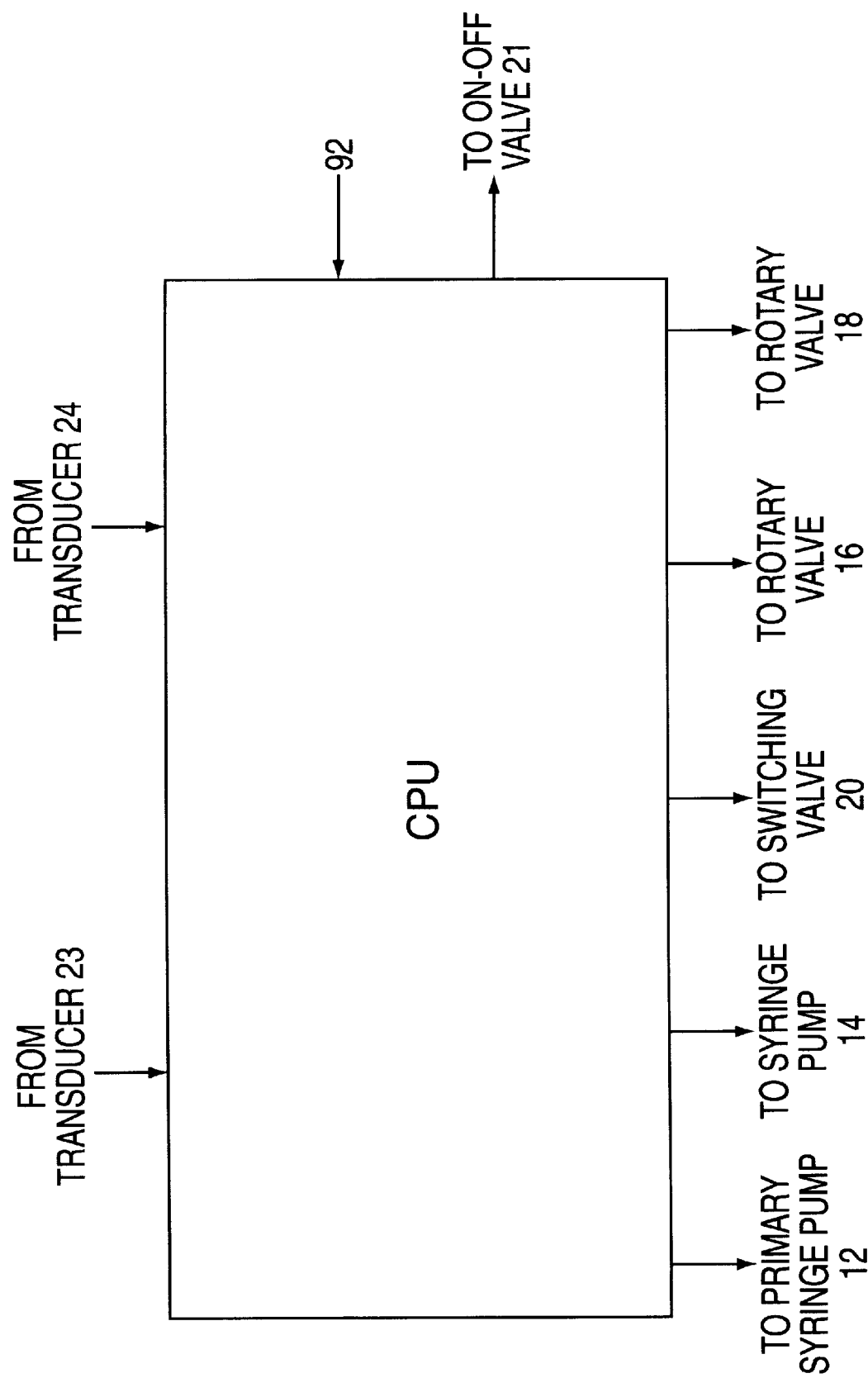
FIG. 5 is a diagrammatical illustration of a central processing unit which may be included in the apparatus embodying the present invention and which figure illustrates the inputs and outputs to and from the central processing unit with respect to the other elements comprising the apparatus of the present invention.

Referring to FIG. 5, the apparatus 10 includes a suitable central processing unit indicated diagrammatically by general numerical designation 92; it will be understood that the central processing unit 92 may be any one of several central processing units known to the art containing a stored program, sometimes referred to in the art as a user file, for operating the other components or elements of the apparatus 10 as described in detail below. Central processing unit 92 will be provided with suitable input signals from the transducers 23 and 24 indicative of the actual running pressure, respectively, of the pressurized wash output 80 from the primary syringe pump 12 and the pressurized solvent output 82 from the syringe pump 14. The central processing unit 92 will provide suitable outputs to operate the primary syringe pump 12, syringe pump 14, rotary valve 16, rotary valve 18, switching valve 20 and on-off valve 21 in the manner described in detail below. The primary syringe pump 12 and syringe pump 14 may each, in the manner known to the art, include a suitable step or stepping motor for operating the syringe pumps in the manner known to the art and in the manner set forth in U.S. Pat. No. 4,347,131 with regard to the operation of the syringe pump 10 by the stepping motor 30 under the control of the central processing unit 58 and as set forth in U.S. Pat. No. 5,637,208 with regard to the operation of the syringe or syringe pumps disclosed therein by the step motor 7A or 7B under the control of the controller 49. The rotary valves 16 and 18 may be operated under the control of the central processing unit 92 in the same manner as the sample injection valve 14 is operated under the control of the central processing unit 58 as set forth in U.S. Pat. No. 4,347,131. More particularly, the respective inner rotors 40 and 44 of the rotary valves 16 and 18 are rotated into or between two positions under the control of the central processing unit 92 and, as described in detail below, are rotated 60° in either the clockwise or counterclockwise direction as also described in detail below. Still further, a pressure will be pre-selected to which the solvent 30 is pre-pressurized and such pre-selected pressure will be determined in accordance with a pressure appropriate for the solvent 30 in eluting the liquid chromatography column contained in the liquid chromatography system 26; such pre-selected pressure will be stored in the program, or user file, of the CPU 92 (FIG. 5).

Figure 2:
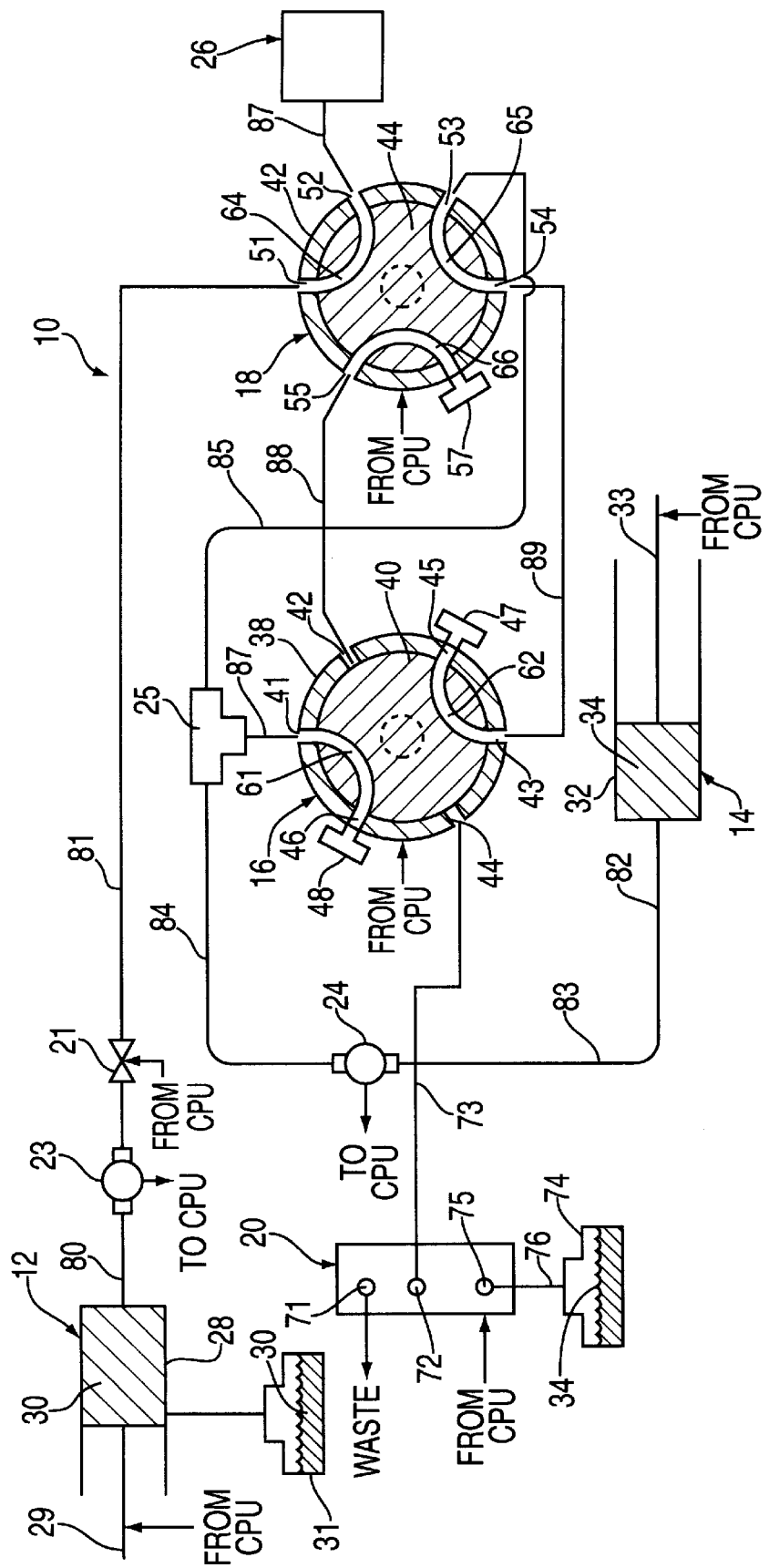

Referring now to FIG. 1, it will be presumed that the elements comprising apparatus 10 described above occupy the positions shown. It will be further presumed that the program stored in the user file contained in the CPU 92 (FIG. 5) will cause the CPU to operate the syringe pump 12 to deliver pre-pressurized solvent 30 to the liquid chromatography apparatus 26 for a period of 200 minutes at a constant flow of 20 micro-liters per minute and to operate the syringe pump 14 to deliver pre-pressurized wash 30 to the liquid chromatography apparatus 26 for a period of 10 minutes at a constant flow of 20 micro-liters per minute; it will be understood that the syringe pumps 12 and 14 will be chosen to have liquid capacities sufficient to deliver the programmed quantities of solvent and wash before all of the solvent and wash contained in the respective syringe pumps are exhausted or delivered to the liquid chromatography system 26. It will be further presumed that under the control of the CPU 92 (FIG. 5), and in accordance with the instructions contained in the program stored in the above-noted user file contained in the CPU, the on-off valve 21 has been closed, that the primary syringe pump 12 has been filled with the solvent 30 from the supply 31, and that the plunger 29 has been advanced into the cylinder 28 to pre-pressurize the solvent 30 to the pre-selected pressure noted above. Under the further control of the central processing unit 92, FIG. 5, the on-off valve 21 will be opened and the pre-pressurized solvent output 80 of the primary syringe pump 12 will be supplied for a period of 200 minutes at a constant flow of 20 micro-liters per minute to the liquid chromatography system 26 through the now open on-off valve 21, transducer 23, liquid transmission line 81, port 51 formed in the outer cylinder 42 of rotary valve 18, internal liquid path 64 provided in the rotor 44 of rotary valve 18 through the port 52 formed in the outer cylinder 42 of rotary valve 18 and the liquid transmission line 87. During the time the primary syringe pump 12 is providing the pre-pressurized solvent 30 to the liquid chromatography system 26, the central processing unit 92, FIG. 5, will operate the switching valve 20 to connect the switching valve port 72 to the switching valve port 71 and the syringe pump 14, under the control of the central processing unit 92, will be operated to drive the plunger 33 into the cylinder 32 to expel any wash 34 remaining in the cylinder 32 from any previous operation and the expelled wash will be transmitted to waste through the liquid transmission line 83, transducer 24, liquid transmission line 84, the through connection through the T-connection 25, liquid transmission line 85, port 53 formed in the outer cylinder 42 of rotary valve 18, internal liquid path 65 formed in the inner rotor 44 of rotary valve 18, the port 54 formed in the outer cylinder 42 of rotary valve 18, liquid transmission line 89, port 43 formed in the outer cylinder 38 of rotary valve 16, internal liquid path 62 formed in the rotor 40 of rotary valve 16, port 44 formed in the outer cylinder 38 of rotary valve 16, liquid transmission line 73, and ports 72 and 71 formed in the switching valve 20. Upon the residual wash in the syringe pump 14 being expelled to waste, under the control of the central processing unit 92, the port 72 of the switching valve 20 is then connected to the switching valve port 75 and the piston 33 of the syringe pump 14, under the control of the central processing unit, will be withdrawn in the cylinder 32 to draw wash 34 from the wash reservoir 74 to refill the cylinder 34. More particularly, the wash 34 will be drawn into the syringe pump 34 from the reservoir 74 through the switching valve ports 75 and 72, the liquid transmission line 73, the port 44 formed in the outer cylinder 38 of rotary valve 16, the internal liquid path 62 formed in the rotor 40 of the rotary valve 16, the port 43 formed in the outer cylinder 38 of rotary valve 16, the liquid transmission line 89, the port 54 formed in the outer cylinder 42 of the rotary valve 18, the inner liquid path 65 formed in the rotor 44, the port 53 formed in the outer cylinder 42 of the rotary valve 18, the liquid transmission line 85, the through connection through the T-connection 25, the liquid transmission line 84, pressure transducer 24 and liquid transmission line 83. The first stage of operation of apparatus 10 is now completed whereupon the second stage illustrated in FIG. 2 is commenced. It will be understood that the operation of switching valve 20 is accomplished before syringe pump transitioning is begun, typically done only once, in what may be referred to as a purging subroutine contained in the user file stored in the CPU 92.

Although the invention as described above expels the wash from syringe 14 prior to refilling the syringe 14 from the wash reservoir 74, the syringe pump 14 can be refilled with wash liquid without expelling the remaining wash liquid from the syringe pump 14 before withdrawing piston 33 of syringe pump 14 to facilitate refilling the cylinder 34.

Referring to FIG. 2, the second stage is commenced by the inner rotor 40 of the rotary valve 16, under the control of the CPU 92, being rotated 60° in the counterclockwise direction to the position shown for the rotor 40 in FIG. 2. Upon the rotor 40 of the rotary valve 16 being rotated in the position shown in FIG. 2, it will be noted that the internal liquid path 61 formed in the rotor 40 is deadheaded against the plugged port 46 due to the plug 48 being inserted into the port 46. It will be understood in FIG. 2 that the inner rotor 44 of the rotary valve 18 remains in its position shown in FIG. 1 and that, under the control of the central processing unit 92, the primary syringe pump 12 continues to deliver the pre-pressurized solvent 30 to the liquid chromatography system 26 at a constant flow as described above with regard to stage 1 and FIG. 1. The transducer 23 will sense the actual running pressure of the solvent 30 flowing in the liquid transmission line 81 and will provide a first signal to the CPU 92 indicative of such sensed pressure; it will be understood that, typically, the actual running pressure in the solvent 30 will be less than the pre-selected pressure to which the solvent 30 was pre-pressurized due to inherent resistance to solvent flow in the apparatus 10 and the liquid chromatography column included in the liquid chromatography system 26. The plunger 33 of the syringe pump 14 will be advanced into the cylinder 32 under the control of the central processing unit 92 to pre-pressurize the wash 34 to the pressure sensed by the transducer 23. More particularly, this is accomplished by the plunger 33 forcing the wash 34 out the output 82 of syringe pump 14 through the liquid transmission line 83, the transducer 24, the liquid transmission line 84, the lateral connection of the T-connection 25, the liquid transmission line 87, the port 41 formed in the outer cylinder 38 of rotary valve 16, and to the deadheaded inner liquid path 61 formed in the rotor 40. It will be understood that in stage 2, the primary syringe pump 12 will continue to be operated under the control of the central processing unit 92 until the solvent 30 has been delivered to the liquid chromatography system 26 at a constant flow of 20 micro-liters per minutes for 200 minutes in accordance with the program stored in the above-noted user file. At the completion of such 200 minutes, stage 3 is commenced.

Figure 3:
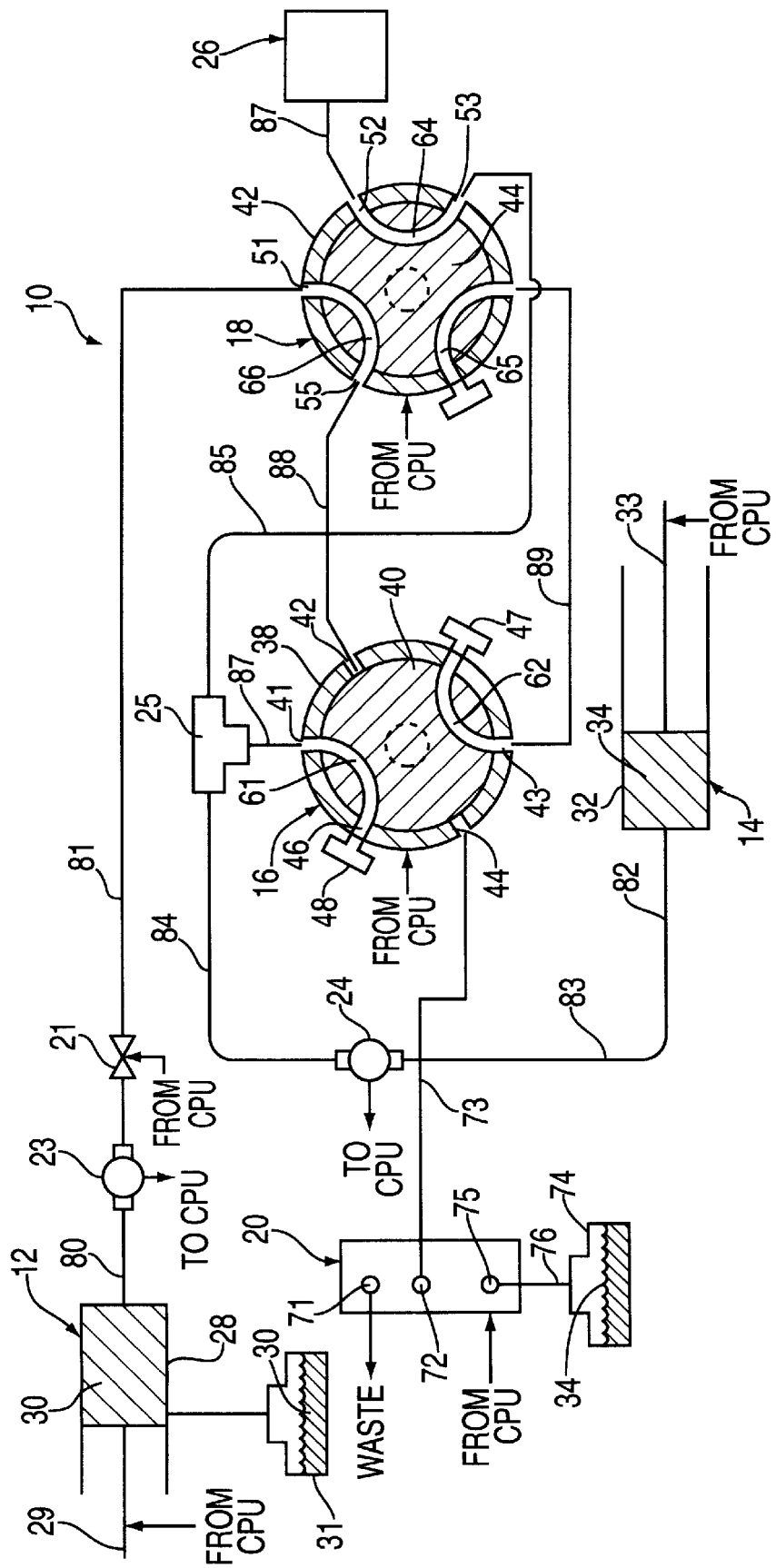

Referring to stage 3 illustrated in FIG. 3, stage 3 is commenced by the central processing unit 92 rotating the rotor 44 of rotary valve 18 clockwise 60° from the position shown in FIGS. 1 and 2 and into the position of the rotor 44 shown in FIG. 3; in stage 3, it will be understood that the inner rotor 40 of the rotary valve 16 remains in the same position of stage 2 shown in FIG. 2. Upon the rotor 44 of rotary valve 18 being rotated into the position shown in FIG. 3, the primary syringe pump 12 will be disconnected from the liquid chromatography system 26 with the output 80 of the primary syringe pump 12 being deadheaded through the on-off valve 21, the transducer 23, the liquid transmission line 81, the internal liquid path 66 formed in the rotor 44 of rotary valve 18, port 55 formed in the outer cylinder 42 of rotary valve 18, liquid transmission line 88 and deadheaded against the rotor 40 of the rotary valve 16 through the port 42 formed in the outer cylinder 38 of rotary valve 16; if desired, any remaining solvent 30 in the syringe pump 12 may be purged while the syringe pump 12 is deadheaded. Simultaneously, the syringe pump 14 under the control of the central processing unit 92 will be operated to drive the plunger 33 into the cylinder 32 and the pre-pressurized wash 34 will be delivered to the liquid chromatography system 26 at a constant flow of 20 micro-liters per minute for a period of 10 minutes (in accordance with the above-noted program in the above-noted user file) through the liquid transmission line 83, the transducer 24, the liquid transmission line 84, the through connection of the T-connection 25, the liquid transmission line 85, the port 53 formed in the outer cylinder 42 of rotary valve 18, the internal liquid path 64 formed in the rotor 44, the port 52 formed in the outer cylinder 42 of rotary valve 18 and the liquid transmission line 87. During such wash delivery, the transducer 24 senses the actual running pressure of the wash 34 in the liquid transmission lines 83 and 84 and provides a second signal to the CPU 92 indicative of such sensed pressure. The primary syringe pump 12 under the control of the central processing unit 92 is de-pressurized by withdrawing the plunger 29 from the cylinder 28, the cylinder 28 is thereafter refilled with solvent 30 from the solvent reservoir 31, and thereafter the plunger 29 is again advanced into the cylinder 28 to pre-pressurize the refilled solvent 30 to the pressure sensed by the transducer 24. This is accomplished by advancing the plunger 29 under the control of the central processing unit 92 to pre-pressurize the solvent 30 re-filled against the above-described deadhead by being transmitted through the on-off valve 21, the transducer 23, the liquid transmission line 81, the port 51 formed in the outer cylinder 42 of rotary valve 18, the internal liquid path 66 provided in the rotor 44, the port 55 formed in the outer cylinder 42 and the liquid transmission line 88 to the port 42 formed in the outer cylinder 38 of rotary valve 18. Under the control of the central processing unit 92, the rotors 40 and 44 of the respective rotary valves 16 and 18 will be rotated back into the positions shown in FIG. 1 and the above-described stages 1, 2 and 3 will be repeated as many times as prescribed in the program stored in the user file contained in the CPU 92.

In brief summary, it will be understood that since the pre-pressurized wash is delivered to the liquid chromatography system at the actual running pressure of the solvent substantially simultaneously with the disconnection of the solvent from the system, and that since the solvent is re-connected to the system at the actual running pressure of the wash, the liquid chromatography system does not experience large excursions in pressurization, de-pressurization and re-pressurization. Further, changes can be made in the solvent and wash without subjecting the system to such pressurization, de-pressurization and re-pressurization excursions.

Figure 4:
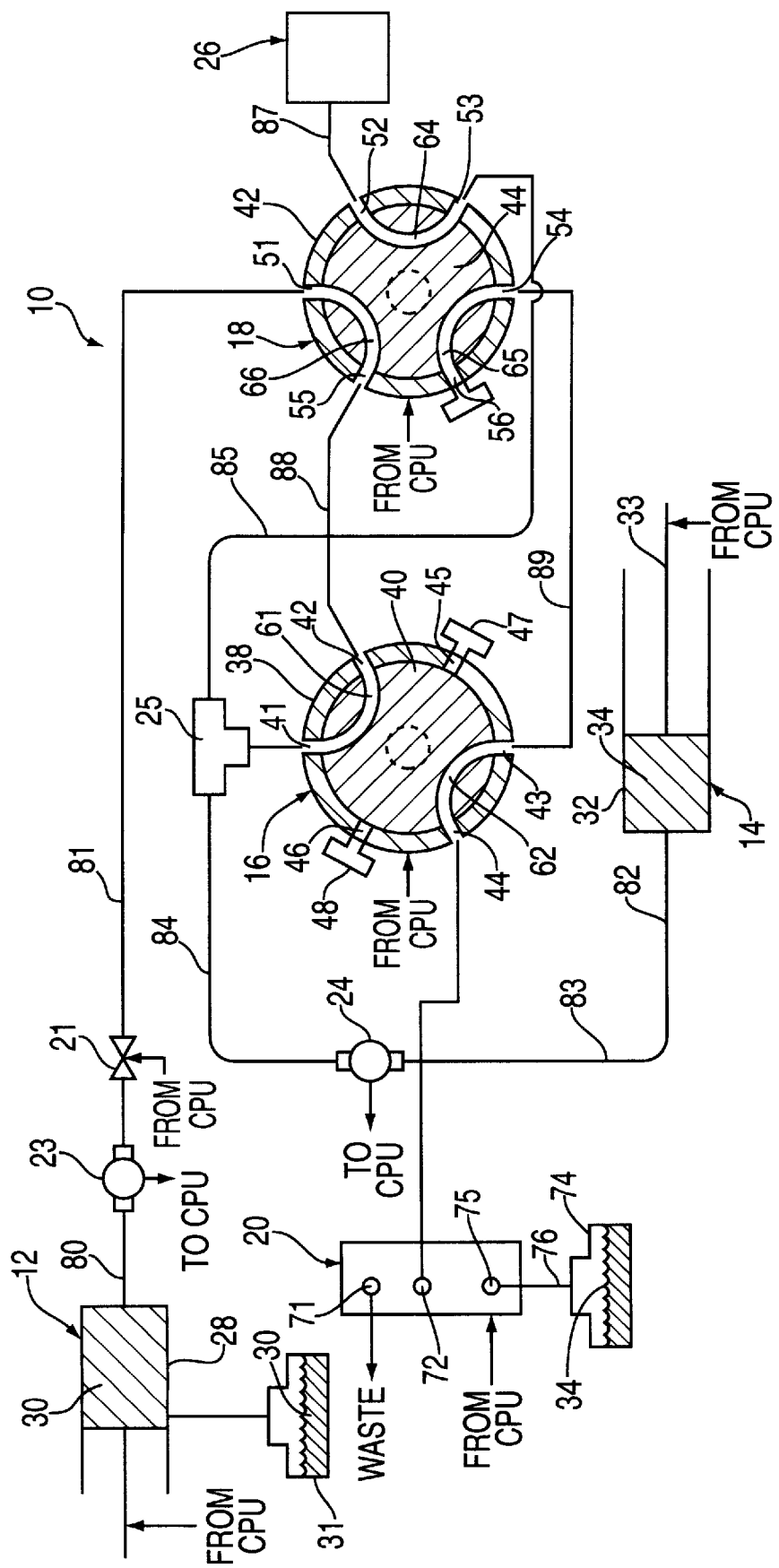
FIG. 4 shows a fourth stage of the present invention which may be utilized to simultaneously provide two flows, for example of solvent to liquid chromatography apparatus, and which step can be used to adjust transducer electronics and for re-equilibration of the liquid chromatography system.

With regard to stage 4 and FIG. 4, this stage is not normally used in the operation of the apparatus 10 of the present invention, but if the wash 34 is replaced with a solvent, this stage can be utilized, if desired, to simultaneously deliver both pre-pressurized solvent from the primary syringe pump 12 and pre-pressurized solvent from the syringe pump 14 to the liquid chromatography system 26. This is accomplished by rotating the inner rotor 40 of the rotary valve 16 clockwise 60° into the position shown in FIG. 4. It will also be understood that in stage 4, FIG. 4, the inner rotor 44 is not moved from the position shown in FIG. 3 but remains in the position shown in FIG. 3. From FIG. 4, it will be understood that upon the inner rotor 40 of rotary valve 16 being rotated in the position shown, the operation of the syringe pump 14 is not affected and syringe pump 14 will continue to supply pressurized solvent 32 to the liquid chromatography system 26 through the same path described above with regard to stage 3 and FIG. 3, but with the inner rotor 40 of rotary valve 16 in the position shown in FIG. 4 the pressurized solvent output 80 from the primary syringe pump 12 will be simultaneously supplied to the liquid chromatography system 26 through the liquid transmission line 81, port 51 provided in outer cylinder 42 of rotary valve 18, internal liquid path 66 provided in rotor 44 of rotary valve 18, port 55 provided in the outer cylinder 42 of rotary valve 18, liquid transmission line 88, port 42 formed in the outer cylinder 38 of the rotary valve 16, internal liquid path 61 formed in the rotor 40 of the rotary valve 12, port 41 formed in the outer cylinder 42, the T-connection 25, liquid transmission line 85, port 53 formed in the outer cylinder 42 of rotary valve 18, internal liquid path 64 formed in the rotor 44 of rotary valve 18, port 52 formed in the outer cylinder 42 of rotary valve 18 and liquid transmission line 87. During stage 4, if desired, it will be understood that the control system associated with central processing unit 92 and the transducers 23 and 24 can be adjusted and calibrated.

It will be understood by those skilled in the art that many variations and modification can be made in the present invention without departing from the spirit and the scope thereof and that the present invention can be used to supply liquids to liquid utilization apparatus other than a liquid chromatography system.

What is claimed is:

1. Apparatus for delivering a substantially constant flow of liquid to liquid utilization apparatus, comprising:

first liquid pumping means and second liquid pumping means; and control means including an interconnected pair of rotary valves and a switching valve for alternately connecting said first liquid pumping means and said second liquid pumping means to respective supplies of first liquid and second liquid to alternately fill said first liquid pumping means with said first liquid and said second liquid pumping means with said second liquid, for alternately operating said first liquid pumping means to pre-pressurize said first liquid and for operating said second liquid pumping means to pre-pressurize said second liquid and for alternately connecting said first liquid pumping means and said second liquid pumping means to the liquid utilization apparatus to alternately deliver said first pre-pressurized liquid and said second pre-pressurized liquid to the liquid utilization apparatus, and for initially operating said first liquid pumping means to pre-pressurize said first liquid to a pre-selected pressure and for operating said second liquid pumping means to pre-pressurize said second liquid to the pressure at which said first liquid pumping means is actually delivering said pre-pressurized first liquid to the liquid utilization apparatus and for thereafter operating said first liquid pumping means to cause said first liquid pumping means to pre-pressurize said first liquid to the pressure at which said second liquid pumping means is actually delivering said pre-pressurized second liquid to the liquid utilization apparatus.

2. The apparatus according to claim 1 wherein said control means operates said first liquid pumping means and said second liquid pumping means to cause said first liquid pumping means and said second liquid pumping means to deliver said first pre-pressurized liquid and said second pre-pressurized liquid to the liquid utilization apparatus at a substantially constant flow.

3. The apparatus according to claim 1 wherein said control means operates said first liquid pumping means and said second liquid pumping means to cause said first liquid pumping means and said second liquid pumping means to deliver said first pre-pressurized liquid and said second pre-pressurized liquid to the liquid utilization apparatus to a substantially constant pressure.

4. Apparatus for delivering liquid to liquid utilization apparatus, comprising:

first liquid delivery means and second liquid delivery means; and control means for:

(i) filling said first liquid delivery means with a first quantity of first liquid;

(ii) operating said first liquid delivery means to pre-pressurize said first quantity of first liquid to a pre-selected pressure and for connecting said first liquid delivery means to the liquid utilization apparatus to cause said first liquid delivery means to deliver said first quantity of pre-pressurized first liquid to the liquid delivery apparatus;

(iii) filling said second liquid delivery means with a second quantity of second liquid while said first delivery means is delivering said first quantity of pre-pressurized first liquid to the liquid utilization apparatus;

(iv) sensing the actual running pressure at which said first quantity of first pre-pressurized liquid is being delivered to the liquid utilization apparatus by said first liquid delivery means prior to delivery of all of said first pre-pressurized liquid to the liquid utilization apparatus to provide a first sensed pressure;

(v) operating said second liquid delivery means to pre-pressurize said second liquid to said first sensed pressure and, prior to the delivery of all of said first quantity of first pre-pressurized liquid to the liquid utilization apparatus by said first liquid delivery means, disconnecting said first liquid delivery means from the liquid utilization apparatus and connecting said second liquid delivery means to the liquid utilization apparatus and to cause said second liquid delivery means to deliver said second quantity of second pre-pressurized liquid to the liquid utilization apparatus;

(vi) refilling said first liquid delivery means with a re-filled first quantity of first liquid while said second liquid delivery means is delivering said second quantity of second pre-pressurized liquid to the liquid utilization apparatus;

(vii) prior to the delivery of all of said second quantity of second pre-pressurized liquid to the liquid utilization apparatus, sensing the actual running pressure at which said second quantity of second pre-pressurized liquid is being delivered to the liquid utilization apparatus to provide a second sensed pressure;

(viii) prior to the delivery of all of said second quantity of second pre-pressurized liquid to the liquid utilization apparatus operating said first liquid delivery means to pre-pressure said re-filled first quantity of first liquid to said second sensed pressure;

(ix) prior to delivery of all of said second quantity of second pre-pressurized liquid to the liquid utilization apparatus disconnecting said second liquid delivery means from the liquid utilization apparatus and reconnecting said first liquid delivery means to the liquid utilization apparatus to cause said first liquid delivery means to deliver said first re-filled quantity of first pre-pressurized liquid to the liquid delivery apparatus;

and (x) re-filling said second liquid delivery means with a re-filled second quantity of second liquid while said first liquid delivery means is delivering said re-filled quantity of first pre-pressurized liquid to the liquid delivery apparatus.

5. The apparatus according to claim 4 wherein said control means is for repeating steps (i) through (ix) for a predetermined number of times.

6. The apparatus according to claim 4 wherein said first liquid delivery means includes a first syringe pump connected to a first reservoir of first liquid and having a first output, wherein said second liquid delivery means includes a second syringe pump having a second output, wherein said control means includes a central processing unit, a switching valve, a first rotary valve, a second rotary valve, a first transducer and a second transducer, and a T-connection, wherein said first output of said first syringe pump is connected to said second rotary valve through said first transducer, wherein said second output of said second syringe pump is connected to said first rotary valve and said second rotary valve through said second transducer and through said T-connector, wherein said second rotary valve is connected to the liquid utilization apparatus, wherein said switching valve is connected to said first rotary valve, wherein said first transducer is connected to said central processing unit to provide a signal indicative of said first sensed pressure, wherein said second transducer is connected to said central processing unit to provide a signal indicative of said second sensed pressure, and wherein said first syringe pump, said second syringe pump, said switching valve, said first rotary valve and said second rotary valve are connected to and under the control of said central processing unit to cause said pre-pressurized first liquid and said pre-pressurized second liquid to be delivered to the utilization apparatus as said.

7. The apparatus according to claim 6 wherein said switching valve includes first, second and third ports, wherein said first port is connected to waste, wherein said second port connected to said first rotary valve and wherein said third port connected to a second reservoir of said second liquid, wherein said first rotary valve includes a stationary, hollow, first outer cylinder providing at least four ports and a first inner rotor residing rotatably in said first outer cylinder and being rotatable under the control of said central processing unit into a first inner rotator position and into a second first inner rotator position, said first inner rotator providing at least two internal liquid paths and said first inner rotor for being rotated into at least first and second positions under the control of said central processing unit to connect said first and second internal liquid paths to different pairs of said at least four ports formed in said first outer cylinder, wherein said second rotary valve includes a stationary, hollow, second outer cylinder providing at least five ports and a second inner rotor residing rotatably in said second outer cylinder and being rotatable under the control of said central processing unit into a first second inner rotator position and into a second second inner rotator position, and said second inner rotator providing at least three internal liquid paths and said second inner rotor for being rotated into at least first and second positions under the control of said central processing unit to connect said third, fourth and fifth internal liquid paths to different pairs of said at least five ports formed in said second outer cylinder.

8. The apparatus according to claim 7 wherein said at least four ports provided in said first outer cylinder comprise fourth, fifth, sixth and seventh ports, wherein said at least two internal liquid paths provided in said first inner rotor comprise a first internal liquid path and a second internal liquid path, wherein said at least five ports provided in said second outer cylinder comprise eighth, ninth, tenth, eleventh and twelfth ports, wherein said at least three internal liquid paths provided in said second inner rotor comprise a third internal liquid path, a fourth internal liquid path, and a fifth internal liquid path, wherein said first output of said first syringe pump is connected to said eighth port of said second outer cylinder, wherein the utilization apparatus is connected to said ninth port of said second outer cylinder, wherein said second output of said second syringe pump is connected to said fourth port of said first outer cylinder and to said tenth port of said second outer cylinder, wherein said fifth port of said first outer cylinder is connected to said twelfth port of said second outer cylinder, wherein said eleventh port of said second outer cylinder is connected to said sixth port of said first outer cylinder, wherein said seventh port of said first outer cylinder is connected to said second port of said switching valve.

9. The apparatus according to claim 8 wherein upon said central processing unit rotating said first inner rotor into said first first inner rotator position and said second inner rotor into said first second inner rotator position:

(i) said first output of said first syringe pump is connected to the liquid utilization apparatus through said eighth port formed in said second outer cylinder, said third fluid path formed in said second inner rotor and said ninth port formed in said second outer cylinder to cause said first syringe pump under the control of said central processing unit to deliver said first limited quantity of said first liquid pre-pressurized to a pre-selected pressure to the utilization device, and said first transducer sensing the actual running pressure of said first liquid to provide said first sensed pressure and to provide a signal to said central processing unit indicative of said first sensed pressure, and (ii) said second output of said second syringe pump is connected to said second port of said switching valve through said tenth port formed in said second outer cylinder, said fourth internal liquid path formed in said second inner rotor, said eleventh port former in said second outer cylinder, said sixth port formed in said first outer cylinder, said second internal liquid path formed in said first inner rotor and said seventh port formed in said first outer cylinder and upon said switching valve connecting said second port of said switching valve to said first port thereof under the control of said central processing unit, said central processing unit operating said second syringe pump to cause said syringe pump to expel to waste any second liquid remaining therein from any prior operation and thereafter said central processing unit operating said switching valve to connect said second port of said switching valve to said third port thereof and said central processing unit operating said second syringe pump to cause said second syringe pump to be filled with said second quantity of second liquid from said second reservoir of second liquid.

10. The apparatus according to claim 9 wherein upon said central processing unit rotating said first inner rotor into said second first inner rotator position and while said second inner rotor remains in said first second inner rotator position, said fourth port formed in said first outer cylinder being connected to said first internal liquid path which is deadheaded and said sixth port formed in said first outer cylinder being connected to said second internal liquid path which is deadheaded to thereby deadhead said second output of said second syringe pump whereupon said central processing unit operates said second syringe pump to pre-pressurize said second liquid to said first sensed pressure against said deadheaded first and second internal liquid paths.

11. The apparatus according to claim 10 whereupon said central processing unit rotating said second inner rotor into said second second inner rotator position while said first inner rotor remains in said second first inner rotator position said eighth port formed in said second outer cylinder being connected by said fifth internal liquid path formed in said second inner rotor to said twelfth port formed in said second outer cylinder to disconnect said first output of said first syringe pump from the liquid utilization apparatus and to deadhead said fifth internal liquid path, and said ninth port formed in said second outer cylinder being connected through said third internal liquid path to said tenth port formed in said second outer cylinder to connect said second output of said second syringe pump to the liquid utilization apparatus whereby said second syringe pump under the control of said central processing unit is operated to provide the liquid utilization apparatus with said second liquid pre-pressurized to said first sensed pressure and said second transducer sensing the actual running pressure of said second liquid to provide said second sensed pressure and providing a signal to said central processing unit indicative of said second sensed pressure, and said central processing unit operating said first syringe pump to de-pressurize said first syringe pump, refill said first syringe pump with re-filled first liquid from said first reservoir and to operate said first syringe pump to pressurize said re-filled first liquid against said deadheaded fifth internal liquid path to pre-pressurize said first liquid to said second sensed pressure.

12. The apparatus according to claim 4 wherein the liquid utilization apparatus is a liquid chromatography system including a liquid chromatography column and said first liquid is a solvent for eluting the liquid chromatography column and wherein said second liquid is a wash liquid for washing the liquid chromatography column.

* * * * *